United States Patent [19]

Julius

[11] 4,071,955

[45] Feb. 7, 1978

[54] HIGHLY ABSORBENT SPONGE

[75] Inventor: Robert P. Julius, New York, N.Y.

[73] Assignee: Nice-Pak Products, Inc., Mount Vernon, N.Y.

[21] Appl. No.: 679,175

[22] Filed: Apr. 22, 1976

[51] Int. Cl.² ............................................. A61C 5/12
[52] U.S. Cl. ................................................... 32/34
[58] Field of Search ................... 32/34, 35, 36, 40 R; 128/290 R, 296, 287, 284

[56] References Cited

U.S. PATENT DOCUMENTS

| 1,997,467 | 4/1935 | Manley | 32/34 |
| 2,613,441 | 10/1952 | Biggs | 32/34 |
| 3,464,415 | 12/1974 | Brownlee | 128/296 |
| 3,816,227 | 6/1974 | Schaar | 128/287 |

*Primary Examiner*—Robert Peshock
*Attorney, Agent, or Firm*—Staas & Halsey

[57] ABSTRACT

A highly absorbent sponge is disclosed which comprises a layer of compressed sponge-like material laminated with at least one layer of woven or non-woven fabric-like material, such as cotton gauze or cotton batting. Alternative embodiments of the invention are shown wherein the laminated layers are held together either by an adhesive or a sewn thread.

4 Claims, 8 Drawing Figures

HIGHLY ABSORBENT SPONGE

BACKGROUND OF THE INVENTION

1. Field of the Invention

The present invention relates to a highly absorbent sponge comprising a lamination of a layer of compresse sponge-like material and a layer of lint-free woven or non-woven fabric. The present invention is intended for use as a dental sponge in the oral cavity to absorb saliva therein and provide bulk for causing a separation of the soft tissues therein. In addition, the sponge of the present invention is intended for use during surgical procedures to absorb large amounts of blood and other fluids.

2. Description of the Prior Art

In the past, the dental profession has employed the use of cotton rolls to absorb saliva in the oral cavity, while work was being performed therein. However, the main disadvantage of cotton rolls is that they do not absorb large volumes of fluid and therefore, must be replaced several times during the dental procedure.

In addition, the cotton rolls tend to leave lint in the oral cavity when they are extracted; and thereby create a condition whereby the lint may be adhesively attached to the dental work and provide minute openings through which decay or other problems may subsequently arise.

A variation of the pure cotton roll is shown in U.S. Pat. No. 1,812,655, wherein a sheet of cotton and a sheet of absorbent paper are wound around each other to form a dental roll with an outer surface of cotton coated with a starch binder. Because the paper absorbs more fluid than cotton, the roll, in the patent, is described as being more absorbent than a pure cotton roll. However, the combination cotton/absorbent paper cotton roll has a disadvantage in that it does not expand as it absorbs saliva. A further disadvantage of both the cotton/absorbent paper roll and pure cotton rolls is that they require a large amount of storage space, with respect to the amount of fluids which they are able to absorb.

SUMMARY OF THE INVENTON

The highly absorbent sponge of the present invention is intended for use by dentists to absorb saliva and other fluids present in the oral cavity during a dental procedure therein, and to provide bulk for separating the soft oral tissues from the area undergoing the dental procedure. Similarly, the sponge of the present invention is intended for use by the medical profession in general where large amounts of blood or other fluids are required to be absorbed.

The sponge of the present invention comprises a layer of sponge-like material, such as cellulose, compressed to about one-fifth its original size, and at least one layer of lint-free woven or non-woven fabric-like material. Several embodiments of the present invention illustrate a layer of fabric-like material affixed to one side of the sponge-like material. Several other embodiments of the present invention illustrate a layer of fabric-like material affixed to each side of the layer of sponge-like material. In each of the embodiments of the present invention, the layers are held together by either an adhesive, applied between each layer, or by a thread, sewn through all of the layers.

When exposed to fluid, the sponge of the present invention expands to several times its original size. Therefore, if the layers of the sponge are held together by an adhesive, the sponge-like material expands to its full capacity, in a normal manner. On the other hand, if the layers of the sponge are held together by a thread, sewn through all of the layers in a series of stitches running in a line extending the length of the sponge, it assumes an approximately cylindrical shape when it absorbs fluid and expands.

The sponge of the present invention has the advantage of being able to absorb three to five times as much fluid as conventional cotton sponges used by dentists and others.

The sponge of the present invention has an additional advantage in that the sponge-like material and the fabric-like material are lint-free so that no lint is left in the oral cavity when it is employed as a dental sponge.

The sponge of the present invention has a still further advantage when employed as a dental sponge in that since the sponge-like material is compressed to about one-fifth its original size, it requires much less storage space than conventional cotton sponges, and in addition, upon expansion in the oral cavity, provides an even greater separation of oral tissues from the area undergoing the dental procedure.

One object of the present invention employed as a dental sponge is to provide for greater absorption of fluids in the oral cavity than provided by dental rolls of the prior art.

Another object of the present invention is to provide a dental sponge having sufficient bulk so as to cause adequate separation between oral tissues adjoining the area undergoing the dental procedure.

A further object of the present invention is to provide a dental sponge that does not leave lint in the oral cavity which could cause future problems such as decay.

A still further object of the present invention is to provide a dental sponge which is smaller than the dental sponges of the prior art, so as to require less storage space, and yet which has the capability of expanding when placed in the oral cavity, so as to provide the bulk for separation of oral tissues as described above.

A still further object of the present invention is to provide a relatively thin surgical sponge that is highly absorbent and expands in size as it absorbs blood or other fluids.

DESCRIPTION OF THE PREFERRED EMBODIMENTS

The four illustrated embodiments of the highly absorbent sponge of the present invention shown in FIGS. 1 through 6, comprise a layer of sponge-like material 4 and a layer of fabric-like material 2 in two of the embodiments, and a layer of sponge-like material 4 and layers of fabric-like materials 2 and 6 in the other two embodiments. The sponge-like material 4 is preferably cellulose, highly compressed in about one-fifth its normal thickness, and capable of absorbing a large volume of fluid. Upon absorbing a large volume of fluid, the material 4 expands to several times its compressed size. The fabric-like materials 2 and 6 are preferably thin layers of woven materials such as cotton gauze or non-woven materials such as cotton batting. The main function of the fabric like materials 2 and 6 is to provide bulk to the sponge when it is employed as a dental sponge, for instance, and first inserted into the oral cavity. The sponge of the present invention has an added essential characteristic of being lint-free, so as not to leave lint in an oral cavity when it is employed as a dental sponge and is extracted from the oral cavity. Both the sponge-like material 4 and the fabric-like materials 2 and 6 are preferably non-toxic, sterile and remain permanently affixed to each other when the sponge absorbs fluid, such as saliva or blood.

The highly absorbent sponge of the present invention is discussed in the following four embodiments.

Figure 1:
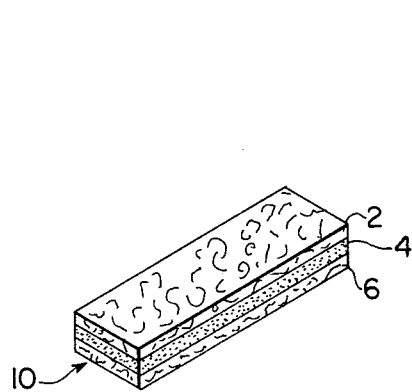
FIG. 1 is a perspective view illustrating the embodiment of the highly absorbent sponge of the present invention in which three layers of material are held together by an adhesive.
Figure 1A:
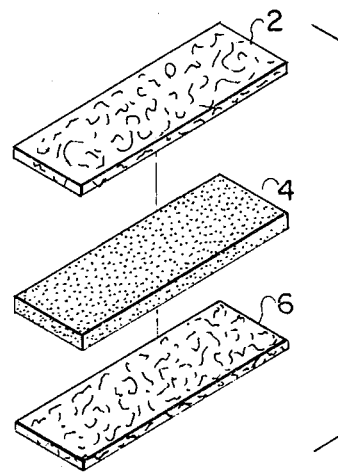
FIG. 1A is an exploded perspective view illustrating the embodiment as shown in FIG. 1.

A first embodiment is shown in the perspective view of FIG. 1 and in the exploded perspective view of FIG. 1A. The sponge 10 consists of three layers of materials; i.e., a layer of fabric-like material 2 affixed to one surface of a layer of sponge-like material 4 and a layer of fabric-like material 6 affixed to the opposite surface of the layer of sponge-like material 4. The aforesaid layers 2, 4 and 6 are held together by an adhesive which preferably has the properties of being both non-toxic and insoluable in water, blood or saliva. It is apparent that, during assembly, adhesive is either applied to both surfaces of the layer of sponge-like material 4 or to the contacting surface of each of the fabric-like materials 2 and 6 which are to be affixed to the layer of sponge-like material 4.

Figure 2:
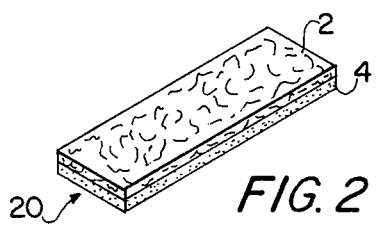
FIG. 2 is a perspective view illustrating another embodiment of the highly absorbent sponge in which two layers of materials are held together by an adhesive.

A second embodiment of the sponge of the present invention is shown in FIG. 2, wherein there are two layers of materials: a fabric-like material 2 is affixed to one planar surface of the sponge-like material 4. The layers are held together by an adhesive such as described in the first embodiment above. This embodiment of the present invention is employed where less bulk and high absorption are desired.

Figure 3:
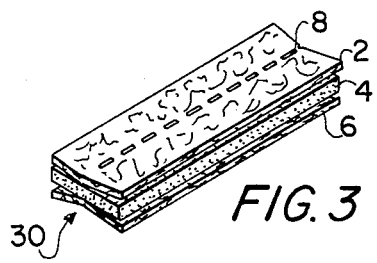
FIG. 3 is a perspective view illustrating a further embodiment of the highly absorbent sponge in which three layers of materials are sewn together.

A third embodiment of the sponge of the present invention is shown in FIG. 3, wherein the sponge 30 comprises a layer of sponge-like material 4, a fabric-like material 2 affixed on one surface of the sponge-like material 4 and a fabric-like material 6 affixed on the opposite surface of the sponge-like material 4. The three layers are held together by a thread 8 stitched along a central line portion of the sponge 30.

Figure 3A:
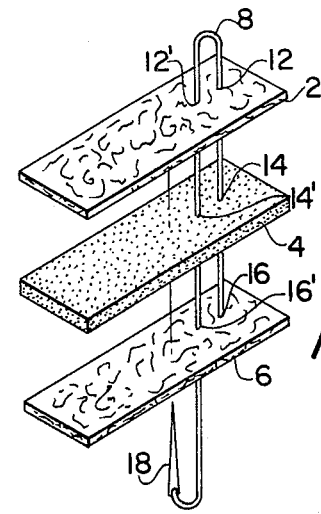
FIG. 3A is an exploded perspective view illustrating the embodiment of the highly absorbent sponge shown in FIG. 3.

FIG. 3A illustrates the stitching of the thread 8 in greater detail. The thread 8 is drawn, by a needle means 18, through to define a hole 16 in the fabric-like material 6, a hole 14 in the sponge-like material 4 and a hole 12 in the fabric-like material 2. The thread 8 is then drawn, by the needle means 18, through to define a hole 12' in the fabric-like material 2, a hole 14' in the sponge-like material 4, and a hole 16' in the fabric-like material 6. This process is continued until the stitching of the thread 8 is complete. In this example, the stitched thread 8 preferably lies along a line centrally lengthwise in the sponge 30, although other patterns of stitching may be used.

Figure 4:
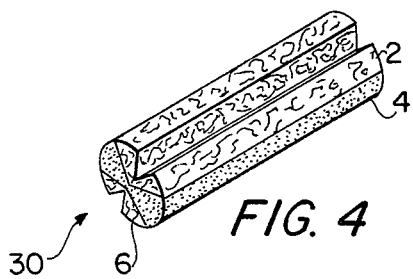
FIG. 4 is a perspective view of the embodiment of the sponge in FIG. 3, illustrating the approximately cylindrical shape the sponge assumes when it absorbs fluid.

In this embodiment shown in FIGS. 3, 3A and 4, the sponge 30 assumes an approximately cylindrical shape when it absorbs fluid. The sponge-like material 4 and the fabric-like materials 2 and 6 expand with the fluid, except where expansion is prevented by the stitched thread 8. The resulting shape of the sponge 30 approximates a cylindrical roll, expanded in size with respect to its non-absorbed state.

Figure 5:
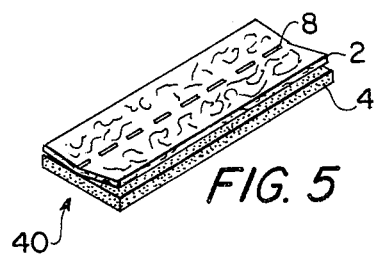
FIG. 5 is a perspective view showing still another embodiment of the highly absorbent sponge of the present invention wherein two layers of materials are sewn together.

A fourth embodiment of the sponge of the present invention is illustrated in FIG. 5. In this embodiment, the sponge 40 consists of two layers; i.e., a fabric-like material 2 being affixed to one planar surface of the songe-like material 4 by a stitched thread 8. In this example, the thread 8 is stitched along a line which is preferably centrally lengthwise to the sponge 230, although a variety of other patterns may be used. The stitching of the thread 8 is accomplished in a manner similar to that described in the third embodiment shown in FIG. 3A.

Figure 6:
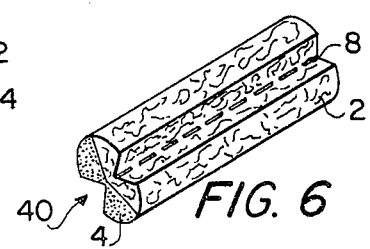
FIG. 6 is a perspective view of the embodiment of the sponge, shown in FIG. 5, illustrating the approximately cylindrical shape the sponge assumes when it absorbs fluid.

FIG. 6 shows the approximately cylindrical shape the sponge 40 assumes when it has absorbed fluid. The sponge-like material 4 and the fabric-like material 2 expand freely toward their outer edges, but are constricted in their expansion by the stitched thread 8, thereby causing the sponge 40 to approximate a cylinder.

It is noted that the choice between the three layered embodiments and the two layered embodiments shown above, depend upon the amount of bulk required for each dental or medical/surgical procedure. Necessarily, the three layered embodiments of the sponge of the present invention provide an initial separation between oral tissues which is greater than the separation provided by the two layered embodiments.

It will be apparent that many modifications and variations may be effective without departing from the scope of the novel concept of this invention. Therefore, it is intended by the appended claims to cover all such modifications and variations which fall within the true spirit and scope of the invention.

What is claimed is:

1. A highly absorbent sponge for use as a dental sponge in oral cavities comprising:
    means so less storage space than normal is required when in non-use and yet is greatly expandable during use so as to absorb three to five times the fluid and also to provide greater separation of oral tissues including;
    a layer of highly absorbent cellulose sponge material of elongated shape and of sufficient smallness to easily fit within a person's mouth,
    means for attachment of at least one layer of woven fabric-like outer material to a plane surface of said sponge material along a longitudinally extending center line thereof,
    said layer of woven fabric-like material being substantially lint free so lint will not be left in the oral cavity when in use as a dental sponge, and said longitudinal center attachment means permitting great expansion along the outer edges of both said sponge material thereby providing and said woven-like material for greater separation of the soft oral tissues during use as a dental sponge than the normal cotton roll.

2. The structure set forth in claim 1, together with a second layer of woven fabric-like material being affixed on an opposite plane surface of said sponge material from said first layer of woven fabric-like material and likewise being affixed by means of the longitudinal extending center attachment means thereof.

3. A structure as in claim 2, wherein said means for attachment of said first and second layers of woven fabric-like material to said first and second surfaces of the sponge material is a thread secured through said layers along the centrally located axis thereof for permitting the outer edge expansion of both layers of woven fabric-like material as well as the cellulose sponge layer for the increased separation of oral tissues during use of the sponge.

4. A sponge as in claim 3, wherein all layers are sterile.

* * * * *

UNITED STATES PATENT AND TRADEMARK OFFICE
CERTIFICATE OF CORRECTION

PATENT NO. : 4,071,955
DATED : February 7, 1978
INVENTOR(S) : Robert P. Julius

It is certified that error appears in the above-identified patent and that said Letters Patent are hereby corrected as shown below:

Column 1, line 5, "compresse" should be -- compressed --;
Column 4, line 23, "songe" should be -- sponge --;
Column 4, line 25, "230" should be -- 30 --;
Column 5, line 3, delete "thereby providing";
Column 5, line 4, after "material" insert -- thereby providing --;
Column 5, line 5, after "tissues" insert -- than the normal cotton roll --;
Column 5, line 6, delete "than the normal cotton roll".

Signed and Sealed this

Twenty-fifth Day of July 1978

[SEAL]

Attest:

RUTH C. MASON
*Attesting Officer*

DONALD W. BANNER
*Commissioner of Patents and Trademarks*